United States Patent [19]

Piteau et al.

[11] 4,210,598
[45] Jul. 1, 1980

[54] PROCESS FOR THE INDUSTRIAL SYNTHESIS OF VINYL AND ISOPROPENYL CHLOROFORMATE AND THIOCHLOROFORMATE

[75] Inventors: Marc D. Piteau, Mennecy; Thierry A. Malfroot, Saint Germain les Corbeil, both of France

[73] Assignee: Societe Nationale des Poudres et Explosifs, Paris, France

[21] Appl. No.: 876,688

[22] Filed: Feb. 10, 1978

[30] Foreign Application Priority Data

Feb. 25, 1977 [FR] France .................................. 77 05641

[51] Int. Cl.² ..................... C07C 154/00; C07C 68/02
[52] U.S. Cl. ................................... 260/455 B; 260/463
[58] Field of Search ............................. 260/463, 455 B

[56] References Cited

U.S. PATENT DOCUMENTS

| 2,337,172 | 12/1943 | Wojcik | 260/463 |
| 2,377,085 | 5/1945 | Kung | 260/463 |
| 3,118,862 | 1/1964 | Schaefgen | 260/30.4 N |

FOREIGN PATENT DOCUMENTS 1129229  11/1967  United Kingdom ..................... 260/463

OTHER PUBLICATIONS

M. P. Matuszak, Journal of the American Chemical Society, 56, 2007 (1934).
L. Lee, Journal of Organic Chemistry, 30, 3943 (1965).
Beak et al., Journal of Organic Chemistry, 38 (16), 2771 (1973).
Marahashi et al., Bulletin of the Chemical Society of Japan, 38 (11), 1905 (1965).

*Primary Examiner*—Henry R. Jiles
*Assistant Examiner*—Robert C. Whittenbaugh
*Attorney, Agent, or Firm*—Bucknam and Archer

[57] ABSTRACT

The invention relates to a process for the industrial scale synthesis of vinyl and isopropenyl chloroformates and thiochloroformates.

According to the invention, phosgene or thiophosgene is reacted, at between 20° and 70° C., with a mercury salt $XHg(CH_2CRO)$, in which $X=Cl$ or $-CH_2CRO$, where $R=H$ or $CH_3$, in the presence of a solvent or a mixture of solvents having a dielectric constant greater than 10. The process can also be carried out using a mixture of the above solvents with a solvent which is not effective by itself (solvent of low polarity) but which is inexpensive. The yields achieved can exceed 90%.

10 Claims, No Drawings

PROCESS FOR THE INDUSTRIAL SYNTHESIS OF VINYL AND ISOPROPENYL CHLOROFORMATE AND THIOCHLOROFORMATE

The present invention relates to a process for the synthesis of compounds of the general formula

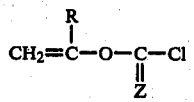

in which R=H or CH$_3$ and Z=O or S.

M. M. MATUSZAK, Journal of the American Chemical Society, 56, 2,007 (1934), would have synthesized isopropenyl chloroformate by the action of phosgene on acetone, at ordinary temperature, with an extremely low yield. However, this process cannot be repeated. As a result, no process is currently available for preparing isopropenyl chloroformate, although the latter is of obvious value because it is a polymerisable molecule possessing a reactive end.

As far as we are aware, no processes are known which make it possible to synthesize vinyl and isopropenyl thiochloroformate.

Vinyl chloroformate is a compound of considerable value, especially as a monomer and as a synthesis intermediate. However, despite the substantial efforts made by numerous firms, nobody has hitherto succeeded in producing this compound by an economic process which would make it possible to exploit its promising possibilities efficiently in industry.

This molecule was first synthesized by F. E. KUNG in 1945. The synthesis, which is described in U.S. Pat. No. 2,377,085, consists in hydrolysing glycol bischloroformate at 450° C. The yield is only 11%.

It was necessary to wait almost twenty years before SCHAEFGEN, in U.S. Pat. No. 3,118,862 of 1964, and LEE, in the Journal of Organic Chemistry 30, 3,943 of 1965, described processes giving better yields of 30 and, in the best case, 44% respectively. However, the principle of the process was always the same and the improvement in the yield, which is far from satisfactory, was obtained at the expense of operations which were difficult to apply in industry. Nevertheless, despite the high energy required by the pyrolysis (450° C.) and the difficulties of separating the vinyl chloroformate from the other pyrolysis products (60 plates are theoretically required), the process was still being commonly used in 1973, as witnessed by the article of BEAK et al., Journal of Organic Chemistry, 38(16), 2,771.

However, whilst attempting to synthesize divinyl carbonate in 1965, MURAHASHI et al. suggested, in the Bulletin of the Chemical Society of Japan, 38(11), 1,905, that a solution containing vinyl chloroformate in tetrahydrofurane must be formed as an intermediate during the action of phosgene on mercuric diacetaldehyde in accordance with the following equation:

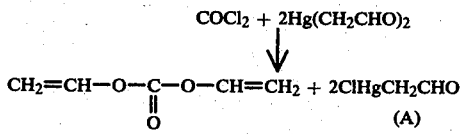

Under the conditions indicated by these authors, the possible yield of vinyl chloroformate was only 19.4% relative to the mercuric diacetaldehyde because phosgene does not react with the mixed mercury salt (A).

If an attempt is made to obtain a total reaction of phosgene with mercuric diacetaldehyde, for example by introducing a tertiary amine, mercuric chloride HgCl$_2$ is indeed obtained; however, once again, only divinyl carbonate remains, as shown by British Pat. No. 1,129,229.

Since the disadvantage of the process suggested by the article of MURAHASHI et al. lies both in the low yield and in the difficulty of stopping the reaction at the vinyl chloroformate stage and, because of the very close boiling points of these compounds, the difficulty of separating the vinyl chloroformate from the tetrahydrofurane, it is possible to consider carrying out the reaction in a solvent which, by virtue of its boiling point, is more favourable for the separation of the desired compound. Unfortunately, despite the fact that the reaction can be carried out successfully in toluene and that the separation is thereby facilitated, the yield is still unacceptably low (22%).

The Applicants have now discovered a process which makes it possible to obtain the vinyl and isopropenyl esters of chloroformic and thiochloroformic acid under conditions which are favourable in industry and with greatly improved yields.

The process according to the invention is characterised in that a chloride, chosen from the group comprising carbonyl chloride and thiocarbonyl chloride, is reacted with a mercury salt having the general formula XHgCH$_2$—CRO, in which R is a hydrogen atom or a methyl group and X is a chlorine atom or the same CH$_2$CRO group, and in that the reaction takes place in a solvent medium comprising a solvent or a mixture of solvents having a dielectric constant which is greater than 10 at 20° C.

The solvents which form the solvent medium, and which, according to the invention, are very suitable by virtue of their relatively high polarity, are preferably those which are inert towards phosgene and thiophosgene, that is to say especially those which do not contain mobile hydrogen atoms. Tertiary amines such as pyridine, and amides used by themselves, such as dimethylformamide and hexamethylphosphorotriamide (HMPT), are also preferably excluded from amongst these solvents. As suitable common solvents having a dielectric constant greater than 10, there may be mentioned halogen-containing aliphatic hydrocarbons, nitrated aliphatic hydrocarbons and nitrile-containing aliphatic hydrocarbons, such as dichloroethane and mononitrated or mononitrile-containing derivatives of lower alkanes, especially nitromethane and nitroethane or acetonitrile, and aromatic derivatives, such as nitrobenzene, nitrotoluenes and 1-chloro-2-nitrobenzene, which are substituted, in positions favouring the polarity of the molecule, by one or more groups, such as halogen atoms or nitro groups, which increase the polarity of the molecule.

However, solvents which are not inert and contain, for example, mobile hydrogens can be used, provided that these said mobile hydrogens are neutralised by means of a stream of chloride; it is sufficient if the product obtained possesses a dielectric constant which is greater than 10 at 20° C. This solution is of little value in view of the considerable consumption of chloride which it involves.

Furthermore, it is of course possible to use a mixture of solvents of low polarity or non-polar solvents with polar solvents, and the medium obtained must have a dielectric constant which is greater than 10 at 20° C. It is also possible to use a mixture comprising two phases of nonmiscible liquids, one of which has a polarity greater than 10, and the other of which is of low polarity or non-polar; for example, a suspension of nitromethane in toluene can be used. Finally, a strongly polar solvent which reacts with chloride, such as HMPT, can be used in solution in a solvent of low polarity, in order to moderate the said reactivity during the synthesis; however, this is not preferred.

The preferred solvents for forming the solvent medium recommended according to the present invention are those which possess, in addition to the above characteristics, a boiling point which is substantially different from, and preferably substantially greater than, the boiling point of the products formed, so as to facilitate the separation of these products by distillation.

The order in which the reactants are introduced is not critical. The phosgene or thiophosgene can be introduced into a solution of mercuric diacetaldehyde or chloromercuric acetaldehyde in one of the solvents or mixtures of solvents described above or, on the other hand, it is possible to introduce the mercury salt into a solution of phosgene in the said solvent or mixture of solvents. This second variant is preferred, especially when the symmetrical mercury salt is used.

The temperature at which the reactants are brought together is preferably relatively low because this bringing together is accompanied by the evolution of heat. During this phase, the reactor is advantageously kept at a temperature of between −80° and 10° C., and preferably between −20° and 0° C.

The actual reaction temperature can be between −20° and +80° C. Generally speaking, the reaction can be run from −80° to +80° C. However, the most favourable temperature is generally between 20° and 60° C.; in fact, the reaction kinetics are slow below 20° C., whereas a competing degradation reaction of the mercury salt is observed above 70° C. Moreover, the temperature can change during the reaction; for example, the reactants can initially be allowed to stand at the temperature at which they are brought together, or at a slightly higher temperature, and the reaction can then be completed at a temperature within the range recommended above.

It is possible for the duration of the operation in which the reactants are brought together not to exceed the time required to pour one reactant into the solution of the other, insofar as the temperature is kept sufficiently low.

The actual reaction time depends on the temperature of the reactor and on the solvent used. In general terms, the reaction time is shorter, the more active (high polarity) is the solvent medium and the higher is the reaction temperature; thus, a reaction time of 3 to 6 hours generally makes it possible to achieve the maximum yield.

The relative proportions required of the various reactants are the stoichiometric proportions, but it is nevertheless preferred to use the phosgene or thiophosgene in an excess of up to 50% relative to the stoichiometric amount, a larger excess being neither disadvantageous nor advantageous. As regards the amount of solvent to be used, it depends on the solvent power with respect to the reactants; nèvertheless, it is generally possible to use from one to ten times more solvent than reactants.

It is very desirable to stir the reaction medium during the actual reaction. In fact, the mercury salt is rather sparingly soluble and the reaction is thus carried out in a heterogeneous phase right up to completion because the mercuric chloride which is finally obtained is even less soluble than the starting salt.

The mercuric diacetaldehyde, chloromercuric acetaldehyde, mercuric diacetone and chloromercuric acetone used as the starting reactants can be prepared, for example, using the method described by LUTSENKO et al. in Dok. Akad. Nauk. SSSR, 102, 97-9 of 1955, which makes it possible to easily achieve a yield greater than 90% and consists in carrying out the reaction having the equation:

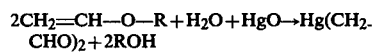
$$2CH_2=CH-O-R+H_2O+HgO\rightarrow Hg(CH_2-CHO)_2+2ROH$$

in which R is a lower alkyl group, in the presence of traces of mercuric acetate and in an aqueous-alcoholic medium.

Since the process according to the invention involves the use of phosgene or thiophosgene, it is appropriate to respect the usual safety conditions. The stirring of the reaction mixture and the temperature will be observed especially during the completion phase. Taking account of the particular properties of the reactants used and those of the product which is finally obtained, which can be identified by NMR, infra-red and elementary analysis, traces of water are advantageously removed both from the starting reactants and from the apparatus.

The yield of the reaction varies according to the different embodiments of the invention, but in all cases it is very substantially greater than the yield of all the processes known hitherto.

In the case of vinyl and isopropenyl chloroformates, the yield of the reaction is greater than 60%, and generally greater than 75%.

Furthermore, it should be noted that the mercuric chloride obtained at the end of the reaction can very easily be regenerated by an alkaline treatment to give mercury oxide which can be used in the preparation of the starting mercury salt.

It is believed that the present invention is entirely surprising to those skilled in the art. In fact, it was not obvious that the choice of the operating conditions which are recommended would make it possible to stop the reaction of mercuric diacetaldehyde with phosgene at the vinyl chloroformate stage, whereas it was well known that this reaction led to the exclusive formation of divinyl carbonate. Furthermore, the present invention clearly contradicts the prior art which agreed that chloromercuric acetaldehyde could only react with phosgene to give vinyl carbonate. Finally, although it was predictable, with regard to the boiling point of vinyl chloroformate, that a heavier solvent would make it possible to facilitate the separation of the compound synthesized, assuming that the reaction could be carried out in this solvent, the high values of the yields to which the present invention leads are totally surprising.

In this respect, it is noted that it will have taken more than 30 years to succeed in discovering an industrial process of synthesis which leads to almost quantitative yields of pure product which is easy to isolate, despite the efforts made by numerous research workers.

Furthermore, no process was known which made it possible to manufacture isopropenyl chloroformate. In fact, all the efforts by applicants to repeat the process of MATUSZAK (mentioned above) have not enabled us to obtain even traces of the said chloroformate. On the other hand, by virtue of the present invention, a process providing perfectly identified isopropenyl chloroformate with an excellent yield is now available.

Likewise, the process according to the invention makes it possible to obtain vinyl thiochloroformate and isopropenyl thiochloroformate which were hitherto unknown and could not be obtained by applying the former processes to the corresponding sulphur-containing starting materials.

The compounds which can be prepared by the process according to the invention are of great value in that they are monomers which carry reactive groups.

Numerous other simple secondary variants of the process which has now been described will readily become apparent to those skilled in the art. In the examples which follow, particular attention has been paid to describing some of the most advantageous variants of the process according to the invention, but it is clear that, in the presence of other economic factors, other more or less advantageous variants can be found which are entirely within the scope of the present invention. In the series of comparison examples, particular attention has been paid to demonstrating the surprising influence exerted by the solvent medium on the yield of the reaction, other things being equal.

EXAMPLE 1

Preparation of mercuric diacetaldehyde 162 g (0.75 mol) of yellow mercury oxide (Merck, purity 99%), 6 g of mercury acetate (Merck, pure), 90 cm$^3$ of ethanol and 30 cm$^3$ of water are placed in a 500 cm$^3$ reactor equipped with a mechanical stirrer, a thermometer, a reflux condenser and a dropping funnel. After stirring for half an hour at ambient temperature, 118.8 g (1.65 mols) of vinyl ethyl ether (Aldrick, purity 99%) are added in the course of 15 minutes; the temperature rises to 50° C. The reaction mixture is filtered whilst hot and left to recrystallise in a refrigerator. After draining the crystals, 193 g of the expected salt, which melts at 90° C. (literature 90°–93° C.), are isolated. The product is stored in a desiccator in the presence of P$_2$O$_5$.

The mercuric diacetaldehyde thus obtained is identified by its NMR spectrum:

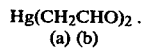
(a) (b)

The type (a) protons are identified by the presence of a 4-proton doublet of doublets centred at 2.62 ppm, and the coupling constant $J_{H(a)H(b)}$ is 6 Hz.

The splitting of the doublet can be attributed to a coupling of the said protons with the $^{199}$Hg isotope which possesses a spin of ½ and a natural abundance of 16.86% (16.6% according to the values deduced from the integration). The coupling constant $J\ ^{199}{}_{Hg}H(a)$ is about 210 Hz.

The type (b) protons correspond to a two-proton triplet at 9.3 ppm.

EXAMPLE 2

Preparation of vinyl chloroformate in nitrobenzene

In this example, a 250 cm$^3$ reactor is used, which is equipped with a mechanical stirrer, a thermometer and a condenser which contains a mixture of acetone and dry ice and is connected to a sodium hydroxide scrubbing column.

120 ml of dry nitrobenzene and 20 ml of phosgene (that is to say 0.21 mol) were placed in the said reactor which had been cooled to −78° C.

30 g (that is to say 0.105 mol) of solid mercuric diacetaldehyde, prepared as described in Example 1, were added rapidly to this solution, at this temperature, by means of a hopper.

The mixture is heated to 55°–60° C. and stirring is maintained at this temperature for 4 hours.

The mixture obtained is then allowed to return to ambient temperature, after which the dry ice condenser is substituted by a small Vigreux column (height 10 cm, diameter 1 cm) surmounted by a reflux head. When the temperature in the boiler is 140° C., 20.2 g of vinyl chloroformate, which distils at 66° C., are collected.

The resulting yield is 71% and the product obtained has the following characteristics:
chlorine content: 32.6±0.2% (theory 33.3)

IR spectrum: bands at 1,780 cm$^{-1}$ (C=O of the chloroformates); 1,650 cm$^{-1}$ (C=C vinyl); 1,160 cm$^{-1}$ (C—O).

NMR spectrum:

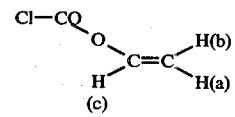

1 type (a) proton: doublet of doublets centred at 4.71 ppm with coupling constants
$J_{H(a)H(b)} = 2.5$ Hz
$J_{H(a)H(c)} = 6$ Hz 1 type (b) proton: doublet of doublets centred at 5 ppm with coupling constants
$J_{H(a)H(b)} = 2.5$ Hz
$J_{H(a)H(b)} = 13.6$ Hz 1 type (c) proton: doublet of doublets centred at 7.68 ppm with coupling constants
$J_{H(c)H(a)} = 6$ Hz
$J_{H(c)H(b)} = 13.6$ Hz

COMPARISON EXAMPLES

A comparison was made of the influence of several representative solvents on the yield of the reaction carried out under the following conditions. 14.325 g (that is to say 0.05 mol) of mercuric diacetaldehyde were introduced into a reactor in a solution of 9 ml (0.125 mol) of phosgene in 50 ml of the dry solvent in question. In each case, this introduction was carried out whilst ensuring that the temperature of the medium did not exceed 0° C.

After having allowed the reactants to react for half an hour at this temperature, the reaction was continued for 4 hours at 60° C.

The following results were obtained:

| Example | Solvents | *Dielectric constant | Yield (%) | Observations |
|---|---|---|---|---|
| 3 | Hexane | 1.8 | very low | unmeasurable traces |
| 4 | Toluene | 2.3 | 22 | |
| 5 | Dibutyl ether | 3.08 | 28.4 | |
| 6 | Dichlorobenzene | 9.93 | 35.7 | |
| 7 | HMPT | 30 | 0 | destruction |
| 8 | Dichloroethane | 10.3 | 66 | |

-continued

| Example | Solvents | *Dielectric constant | Yield (%) | Observations |
|---|---|---|---|---|
| 9 | Nitromethane | 28 | 63 | |
| 10 | Nitrobenzene | 34 | 63.9 | |
| 11 | Acetonitrile | 37.5 | 80.8 | |
| 12 | Dichlorobenzene + acetonitrile | 10< | 43 | (0.05 mol of acetonitrile) |
| 13 | Toluene + dimethylaniline | 10< | 4.3 | (0.5 mol of dimethylaniline) |

*measured at 20° C.

Experiments 3 to 6 reveal that any solvents having a dielectric constant lower than 10 give very moderate yields, whereas the yield is much higher (Experiments 8 to 11) when the said constant is greater than 10. In each of these families, it is found that the yield also improves as the solvent becomes more ionising.

It is seen that, if a small amount of a polarising polar solvent is associated (Experiment 12) with a solvent with low polarity or with a non-polar solvent, the reaction medium obtained does not make it possible to improve the yield decisively if the dielectric constant is lower than 10.

Finally, it is seen that the presence of a tertiary amine in the solvent exerts a disadvantageous influence (Experiment 13).

EXAMPLE 14

Synthesis of vinyl chloroformate from chloromercuric acetaldehyde 245 g (0.878 mol) of chloromercuric acetaldehyde in 800 ml of nitrobenzene were placed in a one liter reactor equipped with a stirrer, a thermometer, a condenser containing a mixture of acetone and dry ice, and a dip tube. The mixture was heated to 60° C. 110 g (1.1 mols) of phosgene gas were added in the course of two hours, whilst keeping the temperature at this level.

Once the addition had ended, the mixture was left for a further two hours at 60° C., whilst stirring.

The volatile constituents (vinyl chloroformate and phosgene) of the mixture obtained were then evaporated off in vacuo and collected in a trap at −78° C. Distillation of the trapped materials, which is carried out at atmospheric pressure, makes it possible to collect 65.2 g of very pure vinyl chloroformate. The overall yield of the reaction is 70%.

EXAMPLE 15

Synthesis of isopropenyl chloroformate

The same apparatus and the same method of operation were used as in Example 14.

The proportions of reactants used are as follows: 117.24 g (0.4 mol) of chloromercuric acetone, 46 g of phosgene (that is to say a molar excess of 15%) and 300 ml of nitrobenzene.

The chloromercuric acetone was obtained by the process of NESMEYANOV which is described in Izvest. Akad. Nauk. SSSR (1949), pages 601–606 (see also Chemical Abstracts, 44, 7,225 c).

35 g of isopropenyl chloroformate were obtained. The yield is 73%.

The isopropenyl chloroformate possesses the following spectral characteristics:

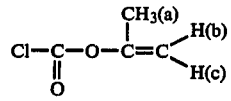

Infra-red spectrum: C=O band at 1,790 cm$^{-1}$; C=C band at 1,685 cm$^{-1}$; C—O band at 1,140 cm$^{-1}$.

Nuclear Magnetic Resonance spectrum: 3 type (a) protons, singlet at 2 ppm; 2 type (b) and (c) protons represented by 2 humps having peaks at 4.75 ppm and 4.89 ppm.

The product obtained has a chlorine content of 29.0±0.2% compared with a theoretical value of 29.45.

Its boiling point is 93° C., which confirms the theoretical value. Its density at 20° C. is 1.007 g/cm$^3$ and its refractive index at the same temperature is 1.415.

By applying the same process to mercuric diacetone, isopropenyl chloroformate possessing the same physical and spectral characteristics was obtained.

EXAMPLE 16

An attempt was made to repeat the reaction described by MATUSZAK in the Journal of the American Chemical Society 56, page 2,007 of 1934.

For this purpose, 70 ml of pure acetone and 7 ml of phosgene were brought together at 25° C. for 15 minutes, 30 minutes, 2 hours and 24 hours respectively. The reaction mixtures obtained were subjected to distillation on a rotating strip. The starting compounds, that is to say phosgene and acetone, were the only compounds obtained in every case.

Furthermore, the infra-red spectra of the reaction mixtures do not show any absorption band other than those of phosgene and acetone.

EXAMPLE 17

10 g of chloromercuric acetaldehyde and 35 ml of nitrobenzene were placed in a 100 ml reactor.

3 ml of thiophosgene (0.04 mol) were added dropwise, in the course of 30 minutes and whilst stirring, to this mixture which had been heated to 60° C.

After the addition, the mixture was left for a further 1 hour at 60° C., whilst maintaining the stirring.

The reaction mixture obtained was distilled in vacuo and the volatile constituents were collected in a cold trap. The mixture comprised vinyl thiochloroformate, divinyl carbonate and a mixed carbonate of the formula:

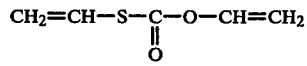

This mixture was subjected to fractional distillation and about 0.5 ml of vinyl thiochloroformate was collected (yield about 10%), which exhibits the following infra-red absorption bands: C=C bond: 1,640 cm$^{-1}$; C=S bond: 1,030 cm$^{-1}$; C—Cl bond: 775 cm$^{-1}$.

What is claimed is:

1. Process for the synthesis of a compound of the general formula

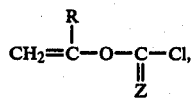

in which R=H or CH$_3$ and Z—O or S, which comprises reacting a chloride, which is a member selected from the group consisting of carbonyl chloride and thiocarbonyl chloride, with a mercury salt having the formula:

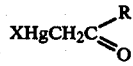

in which R is a hydrogen atom or a methyl group and X is a chlorine atom or the same

group, in a solvent medium comprising a solvent of dielectric constant greater than 10 at 20° C. or a mixture of solvent having a dielectric constant which is greater than 10 at 20° C., at a temperature between +80° C. and −80° C.

2. Process according to claim 1, wherein the solvent medium is a mixture comprising two phases of non-miscible liquids, one of which has a polarity greater than 10, and the other of which is of low polarity or nonpolar.

3. Process according to claim 1 wherein the solvents forming the solvent medium are inert towards phosgene and thiophosgene.

4. Process according to claim 1 wherein the solvent medium comprises at least one polar solvent which has a dielectric constant greater than 10 and is a member selected from the group consisting of halogen-containing aliphatic hydrocarbons, nitrated aliphatic hydrocarbons, nitrile-containing aliphatic hydrocarbons and aromatic hydrocarbons which are substituted, in positions favoring the polarity of the molecule, by at least one substituent which is halogen or nitro.

5. Process according to claim 4, wherein the solvent medium comprises at least one solvent which is dichlorethane, acetonitrile, nitromethane or nitrobenzene.

6. Process according to claim 1, wherein reaction is carried out at between 20° and 60° C. for 3 to 6 hours.

7. Process according to claim 1 wherein the reactants are brought together at between −80° and +10° C.

8. Process according to claim 1 wherein said mercury salt is introduced into a solution of said chloride in the solvent medium.

9. Process according to claim 1 wherein an excess of chloride is used over the stoichiometric amount, and the reaction medium is stirred during the reaction.

10. Vinyl thiochloroformate.